(12) United States Patent
Ichino et al.

(10) Patent No.: US 9,169,160 B2
(45) Date of Patent: Oct. 27, 2015

(54) PROCESS FOR MANUFACTURING HIGH-EXPANSION GYPSUM PLASTER COMPOSITION AND HIGH-EXPANSION GYPSUM PLASTER COMPOSITION OBTAINED BY SAID PROCESS

(71) Applicant: YOSHINO GYPSUM CO., LTD., Tokyo (JP)

(72) Inventors: Yusuke Ichino, Tokyo (JP); Masato Yoshikane, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 0 days.

(21) Appl. No.: 14/423,038

(22) PCT Filed: Aug. 22, 2013

(86) PCT No.: PCT/JP2013/072440
§ 371 (c)(1),
(2) Date: Feb. 20, 2015

(87) PCT Pub. No.: WO2014/064525
PCT Pub. Date: Mar. 6, 2014

(65) Prior Publication Data
US 2015/0218052 A1    Aug. 6, 2015

(30) Foreign Application Priority Data
Aug. 27, 2012   (JP) .................................. 2012-187004

(51) Int. Cl.
| C04B 11/00 | (2006.01) |
| A61C 13/34 | (2006.01) |
| A61K 6/00 | (2006.01) |
| C04B 28/14 | (2006.01) |
| C04B 14/04 | (2006.01) |
| A61K 6/10 | (2006.01) |

(52) U.S. Cl.
CPC ................. C04B 28/141 (2013.01); A61K 6/10 (2013.01); C04B 14/04 (2013.01)

(58) Field of Classification Search
CPC ........... C04B 11/00; A61C 13/34; A61K 6/00
See application file for complete search history.

(56) References Cited

U.S. PATENT DOCUMENTS 2,741,562 A  *  4/1956  Haworth ........................ 106/650
4,234,345 A       11/1980  Fassle

FOREIGN PATENT DOCUMENTS

| JP | 56-155052 | 12/1981 |
| JP | 8-10269 | 1/1996 |
| JP | 2003-339743 | 12/2003 |
| JP | 2004-532062 | 10/2004 |

* cited by examiner

*Primary Examiner* — Paul Marcantoni
(74) *Attorney, Agent, or Firm* — Hamre, Schumann, Mueller & Larson, P.C.

(57) ABSTRACT

An object of the present invention is to provide a high-expansion gypsum composition in which the expansion coefficient of a general purpose dental gypsum material or the like is simply and effectively improved to such an extent that has never been achieved with conventional technologies without using any special material by adding an inexpensive additive even in a small addition amount, and furthermore another object of the present invention is to provide a high-expansion gypsum composition the setting expansion coefficient of which is appropriately controlled so that the contraction of a resin to be used can be precisely dealt with, the high-expansion gypsum composition being useful for manufacturing a reproduction model to be used in manufacturing a "non-clasp denture" having no problem in, for example, occlusion (adaptability). The objects of the present invention are achieved by means of a method for producing a high-expansion gypsum composition, the method producing a gypsum composition having an enhanced setting expansion coefficient by copulverizing in a dry system a powdered gypsum composition containing calcined gypsum as a main component and dihydrate gypsum.

8 Claims, No Drawings

PROCESS FOR MANUFACTURING HIGH-EXPANSION GYPSUM PLASTER COMPOSITION AND HIGH-EXPANSION GYPSUM PLASTER COMPOSITION OBTAINED BY SAID PROCESS

TECHNICAL FIELD

The present invention relates to a method for producing a high-expansion gypsum composition comprising calcined gypsum as a main component and also relates to a high-expansion gypsum composition obtained by the method. More specifically, the present invention relates to a technology by which a high-expansion gypsum composition: that is particularly useful in manufacturing, for example, a non-clasp denture which is one of dental prostheses and is excellent in aesthetic quality; that exhibits a setting expansion coefficient (hereinafter, also simply referred to as "expansion coefficient") clearly higher than that of usual dental gypsum compositions utilized for manufacturing dental prostheses; and in which the expansion coefficient can appropriately be controlled; is simply provided.

BACKGROUND ART

In dental treatment, dental prostheses each having a complicated shape that is adaptable to each patient have been used, and among the dental prostheses, dentures have widely been used. Among the dentures, a so-called partial denture (hereinafter, also simply referred to as "denture") has metal attachments called as clasps and has a structure by which the clasps are fixed to health teeth in such a way that the clasps are hooked to the health teeth. Therefore, there has been an irrational problem that a part of each health tooth to be a grounding surface of the clasps usually has to be cut in order to wear the partial denture. Furthermore, there has also been a problem that the health of the teeth that would be healthy is liable to be impaired because of cutting the teeth or hooking the clasps to the teeth. Moreover, there has been another problem about aesthetic quality that a clasp part is seen by a conversational partner or the like to be found that a person in question wears a denture. The problem about the aesthetic quality is an important problem that should be taken seriously to a person who has to use a denture because the problem can lead to mental illness.

In order to solve these problems once for all, a denture without a clasp which is called a "non-clasp denture" and is excellent in aesthetic quality, the denture being supported by a "fixing part" that substitutes for the clasps and is manufactured from the same material (synthetic resin) as has been used for manufacturing gums for conventional dentures has been developed in recent years, and dentists who handles the "non-clasp denture" have been increasing.

As description will be made later about an outline of manufacturing the "non-clasp denture", when the "non-clasp denture" is manufactured, it is necessary that the denture be manufactured with which a problem of adaptability or occlusion does not arise by manufacturing the "fixing part" that can substitute for the conventional clasps with a synthetic resin. Since the denture chews various kinds of foods with strong force and is used in oral cavity where there is a possibility that the denture is exposed to a gastric acid, polycarbonate resins or the like that are excellent in various properties such as shock resistance have been used as a synthetic resin for manufacturing the fixing part. In the "non-clasp denture", the "fixing part" of the denture is manufactured using a gypsum mold with a polycarbonate resin or the like, and the synthetic resins have a property that contraction occurs during setting (polymerization). Therefore, a teeth model having dimensions for which the contraction of the synthetic resins that occurs during polymerization is taken into consideration in advance is considered to be required in order to manufacture the "non-clasp denture" that is excellent in dimensional accuracy and has no problem in occlusion. Specifically, a reproduction model the size of which is adjusted to somewhat larger than the size of a teeth model which is made of gypsum and is manufactured faithfully based on an impression of teeth taken from a patient in a dentist's office has been manufactured.

For example, the polycarbonate resin that has been used in manufacturing the "non-clasp denture" as a material for manufacturing a gum part including the "fixing part" that substitutes for the clasps is a material in which a large heat contraction (about 0.4 to about 0.7%) occurs during polymerization. Therefore, when the "non-clasp denture" is manufactured using a teeth model made of gypsum as it is, the teeth model manufactured based on an impression actually taken from a patient, the "non-clasp denture" becomes too small and the adaptability becomes poor. The "adaptability" is directly linked to the "occlusion" that is an extremely important element among the properties of the denture to be set and used in oral cavity having keen senses. Furthermore, when the "non-clasp denture" is too small, it is impossible to repair it and it is necessary to remake another one because the "non-clasp denture" has a fatal defect. Therefore, in manufacturing the "non-clasp denture", it is an extremely important matter how to manufacture the aforementioned teeth model in a precise size, the teeth model (hereinafter, also simply referred to as "reproduction model") reproduced so that the size is adjusted to somewhat larger than the size of the teeth model which is made of gypsum and is manufactured using an impression of teeth taken from a patient with the contraction of the resin taken into consideration.

The reproduction model is manufactured by using a high-expansion gypsum composition exhibiting the expansion coefficient higher than that of a gypsum material for manufacturing a usual gypsum model. In addition, use of the gypsum composition having such a large expansion coefficient is not only limited to the case where the above-described "non-clasp denture" is manufactured, but also, for example, the gypsum composition having such a large expansion coefficient is used for manufacturing a so-called full denture (hereinafter, referred to as "artificial teeth") in which a dental plate is manufactured using a resin, and the gypsum composition is widely used for preparing gypsum molds. In the present invention, description is made by taking a case where the "non-clasp denture" is manufactured as a representative example. The reason is that, in this case, since a higher adaptability is required in a sense that the delicate occlusion is required, it becomes necessary to more precisely control the expansion coefficient of the high-expansion gypsum composition particularly according to the contraction of a resin to be used in manufacturing the above-described reproduction model.

Under the above-described circumstances, various high-expansion gypsum compositions in which the expansion coefficient in usual gypsum materials is enhanced in order to deal with the contraction of a resin have so far been proposed. For example, as the gypsum for making an artificial tooth, there has been a proposal (see, Patent Literature 1) on high-expansion gypsum in which the expansion coefficient is enhanced utilizing heat expansion of a resin by adding a granular resin to the gypsum, and there has also been a proposal (see, Patent Literature 2), as a composition that can be used as a material for a dental purpose model, in which a high expansion coefficient with a linear expansion of at least 0.5% can be realized during coagulation or setting by adding a silicate such as silica sol as an inorganic additive to gypsum plaster.

CITATION LIST

Patent Literature

Patent Literature 1: Japanese Patent Laid-Open No. 8-10269
Patent Literature 2: National Publication of International Patent Application No. 2004-532062

SUMMARY OF INVENTION

Technical Problem

However, according to the studies conducted by the present inventors, in the technology described in Patent Literature 2 for example in which a high-expansion property is said to be realized by adding the inorganic additive to the gypsum, the silicate is contained as an additive at an extremely high concentration relative to a gypsum powder, and there is a problem, which should be solved first even though there is an improvement in expansion coefficient, that the material cost increases. Furthermore, the linear expansion that is shown in Examples in Patent Literature 2 is about 0.5 to about 0.6% when the cases where the gypsum powder is coagulated under special conditions are excluded, while the gypsum to which the silicate is not added has a linear expansion of about 0.3%, and the obtained expansion coefficient-increasing effect is not so large considering that a large amount of the silicate is added. This is the same as in the technology described in Patent Literature 1 in which a resin is used as an additive. Moreover, in the technology described in Patent Literature 1, there is a problem that special super hard gypsum (having a linear expansion coefficient of 0.06% at 70° C.) is used in Examples probably because a problem of lowering in strength occurs by allowing the resin to be contained, and there is also a problem that the precision of the linear expansion in heat expansion is generally not so stable as compared with the precision of the linear expansion in setting expansion. As described above, a remarkable increase in expansion coefficient, which is the object of the present invention, has not been able to be realized simply with any of the conventional technologies when applied to any general purpose gypsum, and besides, with a small additive amount.

Accordingly, an object of the present invention is to provide a technology with which a gypsum material the expansion coefficient of which is simply and effectively enhanced relative to, for example, general purpose dental gypsum materials and so on to such an extent that has never been achieved with the conventional technologies can be obtained simply without using any special material by using an inexpensive additive even in a small addition amount thereof. Furthermore, another object of the present invention is to provide a technology capable of appropriately controlling the expansion coefficient of a high-expansion gypsum composition which is also useful for manufacturing a reproduction model to be used in manufacturing, for example, a "non-clasp denture" and which makes it possible to manufacture the "non-clasp denture" having no problem in occlusion (also referred to as "adaptability") by precisely dealing with a problem of contraction of a synthetic resin to be used.

Solution to Problem

The above-described objects are achieved by the following present invention. Namely, the present invention provides a method for producing a high-expansion gypsum composition having an enhanced setting expansion coefficient, the method comprising: a copulverizing step of copulverizing by a dry process a powdered gypsum composition material comprising calcined gypsum as a main component and dihydrate gypsum.

Preferable embodiments of the present invention include the following embodiments. Namely, the powdered gypsum composition material is obtained by externally adding the dihydrate gypsum within a range of 0.01 to 3 mass parts relative to 100 mass parts of the calcined gypsum; the powdered gypsum composition material further comprises fused silica, and the fused silica is externally added within a range of 5 to 30 mass parts relative to 100 mass parts of a total amount of the calcined gypsum and the dihydrate gypsum; a value of linear setting expansion for the gypsum composition after copulverization measured in accordance with Linear Setting Expansion (1) Measurement described in JIS T 6605 (2005) is increased 1.1 to 4.3 times as large as the value of the linear setting expansion for the powdered gypsum composition material before the copulverization by conducting the copulverization in the copulverizing step; and the copulverization is conducted with a dry milling and pulverizing apparatus.

Moreover, as another embodiment, the present invention provides a high-expansion gypsum composition obtained by any one of the above-described methods for producing a high-expansion gypsum composition, wherein a value of linear setting expansion measured in accordance with Linear Setting Expansion (1) Measurement described in JIS T 6605 (2005) is 0.45% or more.

As still another embodiment, the present invention provides a high-expansion gypsum composition obtained by any one of the above-described methods for producing a high-expansion gypsum composition, wherein a value of specific surface area for the gypsum composition material after the copulverization is 2360 to 5040 cm$^2$/g.

A preferable embodiment of the above-described high-expansion gypsum composition includes a high-expansion gypsum composition for being utilized for manufacturing a reproduction model of a teeth model to be used in forming a dental prosthesis.

Advantageous Effects of Invention

According to the present invention, it is possible to allow, for example, a general purpose dental gypsum material to change into a high-expansion gypsum composition that exhibits a high expansion coefficient enhanced to such an extent that has never been achieved with the conventional technologies in a surprisingly effective manner without using any special material by using basically only an inexpensive gypsum material constituted from the calcined gypsum and the dihydrate gypsum used as an additive even when the addition amount of the dihydrate gypsum used as an additive is extremely small, and by simple means of just copulverizing these materials. Furthermore, according to the present invention, it becomes possible to provide a high-expansion gypsum composition the expansion coefficient of which is designed as desired, the high-expansion gypsum composition: being particularly effective in manufacturing, for example, a "non-clasp denture"; making it possible to favorably deal with the problem of contraction of a resin to be used; and making it possible to manufacture a "non-clasp denture" having no problem in occlusion (adaptability).

DESCRIPTION OF EMBODIMENTS

Hereinafter, the present invention will be described in more detail giving preferable embodiments. The present inventors have conducted detailed studies on various additives and addition methods thereof etc. for the purpose of enhancing the expansion coefficient of the gypsum material in an effort to solve the above-described problems of the conventional technologies. As a result thereof, the present inventors have found that the expansion coefficient of the gypsum material can be outstandingly enhanced without using any special material by improving addition and mixing means in which basically dihydrate gypsum is just added to calcined gypsum that is a main component even when the addition amount is small, and have reached the present invention. More specifically, the present inventors have found that the expansion coefficient of a powdered gypsum composition material can be surprisingly enhanced by an extremely simple method in which the powdered gypsum composition material obtained by adding the dihydrate gypsum to the calcined gypsum that is a main component is copulverized in a dry system using a dry milling and pulverizing apparatus such as a ball mill. In addition, the milling and pulverizing apparatus is a pulverizer that pulverizes a substance by force of friction, compression, or the like using a medium.

The present inventors have further found that the novel effect as described below is exhibited in addition to the aforementioned effect when fused silica conventionally known as an additive to enhance the expansion coefficient of a gypsum material is further used as an additive to constitute the powdered gypsum composition material to be used in the present invention. Specifically, for example, when a reproduction model is manufactured using an agar impression material, the occurrence of cracks to the reproduction model can be prevented or the surface state of the reproduction model can be made favorable. In addition, the expansion coefficient in question in the present invention means, as shown previously, the setting expansion coefficient (expansion coefficient) when the calcined gypsum that is a main component is set. Moreover, the setting expansion coefficient of the calcined gypsum for a usual dental model is about 0.3%, and the high-expansion gypsum composition of the present invention means a gypsum composition that exhibits an expansion coefficient higher than the setting expansion coefficient of the calcined gypsum for a usual dental model.

First of all, the outline of manufacturing the "non-clasp denture" is described for the purpose of showing the usefulness of the high-expansion gypsum composition provided by the present invention. When a denture is manufactured in dental treatment, an impression of a part for which a patient is in need is firstly taken using an impression material such as agar or silicon (hereinafter also simply referred to as "impression material"), and then, in accordance with the usual method, a teeth model made of gypsum (hereinafter, referred to as "gypsum teeth model") is made with a gypsum material containing calcined gypsum as a main component. The gypsum teeth model has dimensions that coincide with the dimensions of an impression of the patient's teeth which is taken with the impression material. Next, the gypsum teeth model is set in a flask, a molten impression material such as agar or silicon is poured into the flask, and shaping of a mold is performed by taking out the gypsum teeth model after the impression material is solidified, thereby manufacturing a mold (impression) formed from the impression material. Furthermore, a reproduction model of the previously-formed gypsum teeth model is manufactured by pouring a high-expansion gypsum composition into the obtained mold. In this occasion, the impression material such as agar or silicon used for the formation of the mold has elasticity and therefore can sufficiently be adapted (follow) the expansion caused when the high-expansion gypsum composition poured into the mold is solidified (set). As a result thereof, the reproduction model to be obtained made of the high-expansion gypsum composition has the size somewhat larger by an amount of the expansion as compared with the gypsum teeth model the shape of which is faithfully taken from the impression of the patient's teeth.

The reproduction model having the size somewhat larger as compared with the gypsum teeth model having the dimensions that coincide with the dimensions of the impression of patient's teeth becomes essential in manufacturing a "non-clasp denture" in order to deal with the aforementioned contraction of the resin. And in this case, it is necessary that the extent of making the reproduction model larger be appropriately determined using the reproduction model with the contraction of a resin to form a "fixing part" that performs an equal function to the clasps being taken into consideration. This means that it is desired that the setting expansion coefficient of the high-expansion gypsum composition to be used for manufacturing a reproduction model can precisely be controlled so as to be a desired value in order to be optimally adaptable to the contraction of a resin. Therefore, the present invention intends to obtain a high-expansion gypsum composition in which a high setting expansion coefficient is realized by simple means and to provide a technology with which the expansion coefficient can precisely be controlled so as to be a desired and appropriate value.

Description is made here on the procedure of manufacturing the "non-clasp denture" which is conducted subsequent to the above-described manufacture of the reproduction model. First of all, a void for pouring a resin, which is necessary for forming a gum part including the "fixing part" that substitutes for the clasps from a resin such as a polycarbonate resin using the above-obtained reproduction model is formed in a manner as described below. Specifically, the gum part including the "fixing part" that substitutes for the clasps (hereinafter, simply referred to as "gum part") is formed on the above-described reproduction model by hand using wax that easily melts with hot water. In the occasion, at part or parts where tooth or teeth are lost on the reproduction model, artificial tooth or teeth manufactured separately and made of a resin or ceramic (hereinafter, simply referred to as artificial teeth) are placed, and the gum part is made using the wax while keeping the state in which the artificial teeth are placed.

Next, a gypsum material is poured into a lower side of a flask having a structure that is separable to upper and lower sides, the above-obtained reproduction model which is provided with artificial teeth and a gum part formed from the wax is put on the gypsum that is solidified to some extent, and, while keeping this state, a tube for forming a runner that reaches a wax part is attached. And a gypsum-separating agent is applied after solidification of the gypsum material so as to make the separation of upper and lower parts of the layer where the gypsum-separating agent is applied easy. Thereafter, the gypsum is further poured thereon to cover the upper part of the flask and completely embed the reproduction model in the gypsum. After the gypsum is solidified, the solidified gypsum is put into hot water together with the flask, and only the wax is allowed to be melted and removed. As a result thereof, a gypsum mold inside of which artificial teeth are arranged and in which the void for pouring a resin is formed around the artificial teeth can be made in the flask. The void formed from the gypsum mold is provided in advance with the runner leading to the void, and therefore a molten resin can be injected into the void through the runner at high temperature and high pressure with a resin injection machine. Thereby, the molten resin is filled in the above-described void without space. Thereafter, when the molten resin is solidified, the gums that retain the artificial teeth and the "fixing part" that substitutes for the clasps and works for fixing the gums and the artificial teeth in oral cavity are integrally formed with the resin to obtain a "non-clasp denture".

As mentioned previously, the high-expansion gypsum composition provided by the present invention is extremely useful for manufacturing a reproduction model having desired dimensions, the reproduction model being somewhat larger than the real impression of teeth. Hereinafter, materials to be used in the production method of the present invention and the addition method of the additives will be described in detail.

The powdered gypsum composition material to be used for the production method of the present invention comprises, as essential components, calcined gypsum that is a main component and dihydrate gypsum added to the calcined gypsum, and the powdered gypsum composition material further comprises fused silica added as necessary.

(Calcined Gypsum)

The calcined gypsum means a ½ hydrate of calcium sulfate [$CaSO_4 \cdot \frac{1}{2}H_2O$] and an anhydride of calcium sulfate [$CaSO_4$] and includes a powder of β-type hemihydrate gypsum, α-type hemihydrate gypsum, or type III anhydride gypsum, or mixtures thereof, etc. Any of the above-listed compounds is usable in the present invention, however it is more preferable to use the α-type hemihydrate gypsum in particular taking the strength of the reproduction model and so on to be formed into consideration. Since the calcined gypsum reacts with water to easily change to the dihydrate gypsum, a slurry obtained by adding water to the calcined gypsum and kneading the resultant mixture immediately solidifies when the slurry is injected into a flask or the like. Therefore, the slurry is widely used in manufacturing the aforementioned gypsum teeth model, and the slurry prepared for dental use is sold on the market. The high-expansion gypsum composition that is a target of the present invention may be the same as the material for forming the gypsum teeth model except that the high-expansion gypsum composition of the present invention has a higher setting expansion coefficient than the material for forming the gypsum teeth model, and therefore the calcined gypsum prepared for dental use and sold on the market may be used in the present invention. In addition, the setting expansion coefficient (expansion coefficient) of the calcined gypsum for dental models sold on the market is about 0.3%.

(Dihydrate Gypsum)

In the production method of the present invention, the gypsum composition material comprising the above-described calcined gypsum as a main component and at least dihydrate gypsum is used. The present inventors have found in the process of conducting the studies on a method for increasing the expansion coefficient of the calcined gypsum that the dihydrate gypsum is particularly effective among various additives. The details on this point will be described later.

The dihydrate gypsum means a dihydrate of calcium sulfate [$CaSO_4 \cdot 2H_2O$] and includes natural gypsum, synthesized gypsum, byproduct gypsum obtained as a byproduct in various chemical processes, and so on, and any of the products obtained by coarsely pulverizing these compounds is usable. According to the present invention, by a simple method of improving a pulverizing and mixing method of the calcined gypsum and the dihydrate gypsum using an extremely small amount of the dihydrate gypsum, it becomes possible to obtain a high-expansion gypsum composition in which a high expansion coefficient that has never been achieved in such an extremely small addition amount with any of the conventional technologies in which various additives have been used. Specifically, it is enough to externally add the dihydrate gypsum within a range of 0.01 to 3 mass parts (0.01 to 3 mass % in terms of external addition %) relative to 100 mass parts of the calcined gypsum. More preferably, a gypsum composition material obtained by externally adding, although depending on the desired expansion coefficient, the dihydrate gypsum within a range of 0.1 to 2 mass parts (0.1 to 2 mass % in terms of external addition %) relative to 100 mass parts of the calcined gypsum, furthermore preferably adding the dihydrate gypsum within a range of 0.1 to 1 mass parts (0.1 to 1 mass % in terms of external addition %) relative to 100 mass parts of calcined gypsum may be used. According to the detailed studies conducted by the present inventors, the expansion coefficient-increasing effect is recognized by adding a larger amount of the dihydrate gypsum that is an additive, however when the addition amount becomes larger than 2 mass %, the compressive strength tends to be lowered. On the other hand, in the case where the high-expansion gypsum composition is used for forming a reproduction model that becomes necessary in manufacturing the aforementioned "non-clasp denture", the compressive strength becomes one of the important properties, and therefore it is preferable to add the dihydrate gypsum in an amount within the above-described range.

(Fused Silica)

The fused silica (also called as silica glass, fused quartz, or quartz glass) can further be added to the gypsum composition material to be used in the present invention in addition to the above-described dihydrate gypsum. According to the studies conducted by the present inventors, by blending the fused silica in the gypsum composition material, cracks that may possibly occur to a reproduction model or roughness on the surface of the model can be prevented when the gypsum reproduction model is manufactured by, as described previously, pouring a high expansion gypsum composition provided by the present invention into an agar impression material. The fused silica has conventionally been known as an additive that is capable of increasing the expansion coefficient by being added to a gypsum composition and is also capable of contributing to swelling by absorbing moisture in manufacturing a reproduction model. As the reason why cracks that may occur to the reproduction model or roughness on the surface of the model can be prevented by further using the fused silica as an additive, the present inventors consider that distortion generated in the growth process of a needle crystal of the gypsum as will be described later is alleviated by the fused silica and, as a result thereof, the occurrence of cracks can be suppressed.

It is preferable that the specific use amount of the fused silica added for the above-described purpose is appropriately determined taking the addition amount of the dihydrate gypsum into consideration. As will be described later, when only 1 mass % of the fused silica is externally added relative to the total amount of the calcined gypsum and the dihydrate gypsum, the addition amount of the fused silica is too small from the standpoint of the occurrence of cracks or not in a reproduction model and the occurrence of roughness on the surface of the reproduction model, and the effect of addition has not sufficiently been recognized. On the other hand, it has been confirmed that when the fused silica is externally added in an amount of, for example, 5 mass % or more relative to the total amount of the calcined gypsum and the dihydrate gypsum, the above-described remarkable effect is sufficiently obtained. Moreover, it is preferable from the standpoint of cost for using the fused silica which is more expensive than the gypsum that the upper limit of the addition amount of the fused silica is set to about 30 mass % (about 30 mass % in terms of external addition %) relative to 100 mass parts of the total mass of the calcined gypsum and the dihydrate gypsum, more preferably, about 20 mass parts (about 20 mass % in terms of external addition %).

(Copulverization)

The characteristic of the method for producing a high-expansion gypsum composition of the present invention is that a powdered gypsum composition material comprising the above-described components is copulverized in a dry system. The present inventors have found in the process of conducting studies that, surprisingly enough, the setting expansion coefficient of the material after copulverization is outstandingly enhanced by, basically, copulverizing the calcined gypsum with an additive that is considered to contribute to the expansion of the calcined gypsum. Furthermore, it has been found that an outstandingly small amount of the additive is sufficient in the copulverization. And it has been confirmed that when a material obtained by adding the dihydrate gypsum in particular among various additives to the calcined gypsum is copulverized, a remarkable setting expansion coefficient-improving effect is obtained. With respect to the fact, the present inventors consider that the reason why a large expansion coefficient is obtained is because fine dihydrate gypsum produced by the copulverization forms crystal nuclei when the calcined gypsum is changed to the dihydrate gypsum by hydration, and needle crystals grow from each of the crystal nuclei, which becomes one of the causes for obtaining the large expansion coefficient. According to the studies conducted by the present inventors, the fine crystal nuclei of the dihydrate gypsum become capable of keeping higher activity by conducting the copulverization as compared in the case of pulverizing the dihydrate gypsum alone separately, thereafter adding the pulverized dihydrate gypsum to the calcined gypsum, and mixing the resultant mixture. In addition, the present inventors have conducted studies on the change in the particle size of the powdered gypsum composition material before and after the copulverization, however a large difference in the particle size distribution has not been recognized although particles having a small particle size tend to increase slightly probably because the material having a small particle size has been used from the beginning. Moreover, as a result of measuring the specific surface area (hereinafter, also referred to as "BSA value") of the gypsum composition material before and after the copulverization by a Blaine air permeability powder size meter, it has been confirmed that the value of the specific surface area becomes slightly larger. As to whether the material is copulverized or not according to the present invention (namely, as to whether the effect according to the present invention is exhibited or not), it can be inferred that the copulverization according to the present invention is conducted when the BSA value after the copulverization has become larger by 100 cm$^2$/g or more as compared with the BSA value before the copulverization.

As a specific method for conducting copulverization, it is preferable to conduct the copulverization with a dry milling and pulverizing apparatus. More preferably, the pulverization with a ball mill conducting pulverization using a medium such as a metal or ceramic ball having a diameter of about 10 to about 50 mm is preferable. The pulverization time differs depending on the amount of a substance to be pulverized, the pulverization facility, the material quality, size, weight, or the like of the medium to be used for the pulverization, however, for example, the exhibition of the pulverization effect has been confirmed by the pulverization for about a few minutes, and in the case where the copulverization is conducted for about 3 hours, the remarkable copulverization effect has surely been obtained. In the present invention, the copulverization has been conducted with a ball mill using, as a medium, a ceramic ball having a diameter of 30 mm. As a result thereof, it has become possible to outstandingly increase the expansion coefficient. More specifically, the value of the linear setting expansion for the gypsum composition after the copulverization has been able to be increased 1.1 to 4.3 times as large as the value of the linear setting expansion for the gypsum composition material before the copulverization, where the value of the linear setting expansion is measured in accordance with Linear Setting Expansion (1) Measurement described in JIS T 6605 (2005). Further more specifically, the gypsum composition having a value of the linear setting expansion of 0.45% or more, and even further the gypsum composition material having a value of the linear setting expansion of 1.0% or more has been able to be obtained. Regarding this point, detailed description will be made with Examples.

To the high-expansion gypsum composition of the present invention, for example, a setting adjustment agent such as a setting accelerator or a setting retarder, and an additive such as an expansion suppressing agent, a dispersant, or a pigment can appropriately be added as necessary in addition to the aforementioned components within a range that does not impair the intended purpose. These additives can be added before copulverizing the powdered gypsum composition material, namely these additives can be copulverized together with the powdered gypsum composition material, and these additives can also be added after copulverizing the powdered gypsum composition material, namely these additives can also be added separately to the high-expansion gypsum composition.

EXAMPLES

Hereinafter, the present invention will be described specifically giving Examples and Comparative Examples. In addition, "parts" and "%" in the following description are based on mass unless otherwise noted.

<Copulverization Conditions>

In the following studies, a ball mill having a mill volume of 13 L was used as a pulverization apparatus for copulverizing gypsum composition materials. With respect to the copulverization conditions, the copulverization was conducted using, as a ball, a ceramic having a ball diameter of 30 mm with a total weight of the ball being 6 kg, and using 3 kg of calcined gypsum (α-type hemihydrate gypsum) and each additive as gypsum composition materials to be copulverized.

<Pulverization of Calcined Gypsum>

The specific surface area (BSA value) before pulverization was measured for the calcined gypsum that was used for the tests to obtain a value of about 2000 to about 2200 cm$^2$/g. And the pulverization was conducted using the ball mill described previously under the conditions described previously for 3 hours, and then the BSA value for the sample after the pulverization was measured to obtain a value of 3100 to 3300 cm$^2$/g.

Example 1 and Comparative Example

<Study on Effects Obtained by Copulverization of Calcined Gypsum with Dihydrate Gypsum—Part 1>

Each powdered gypsum composition material obtained by externally adding dihydrate gypsum (manufactured by Yoshino Gypsum Co. Ltd.: product name Tiger Calcee) in each amount as shown in Table 1 to the calcined gypsum previously used was copulverized under the aforementioned conditions for 3 hours. The resultant pulverized products (exploited samples obtained by conducting copulverization) and samples (comparative samples obtained without conducting copulverization) each obtained by mixing, by hand, the calcined gypsum with the dihydrate gypsum in the same amount as in each of the pulverized products, the samples being used for comparison with the pulverized products were prepared. And the setting expansion coefficient was measured for each sample by the following method. First of all, the sample was put into 25 mass parts of water relative to 100 mass parts of the calcined gypsum in 15 seconds, and the resultant mixture was stirred with a spatula for 1 minute to manufacture a gypsum slurry. A gypsum-solidified body was made by pouring the gypsum slurry thus manufactured into a mold, and the compressive strength at 1 hour after pouring the gypsum slurry and the setting expansion coefficient at 2 hours after pouring the gypsum composition were measured by the following methods respectively.

(Compressive Strength Test)

The compressive strength was measured by the following method in accordance with the compressive strength test described in JIS T 6605 (2005). First of all, a cylindrical mold having a height of 40 mm and an inner diameter of 20 mm was prepared in the center of a glass plate, and the above-described gypsum slurry was poured into the mold. Next, a glass plate was pressed on the upper surface before the gloss disappeared from the surface of the gypsum slurry. The sample was taken out from the mold at 45 minutes after the start of mixing, and the sample was stored under the environmental conditions of a temperature of 23±2° C. and a relative humidity of 50±10%. And then, the compressive strength was measured with a compressive strength test apparatus at 60 minutes after the start of mixing (rate of loading 5 kN/min).

(Measurement of Expansion Coefficient)

The value of the linear setting expansion was measured in accordance with Linear Setting Expansion (1) Measurement described in JIS T 6605 (2005).

(Evaluation Results)

The results obtained by conducting the above-described tests are separately shown in Table 1 and Table 2 for exploited samples and comparative samples respectively.

It was able to be confirmed from the comparison of Table 1 with Table 2 that the value of the linear setting expansion became large by conducting the copulverization. Furthermore, with respect to the addition amount of the dihydrate gypsum to the calcined gypsum required for enhancing the value of the linear setting expansion, the effect of enhancing the value of the linear setting expansion was surely recognized when the addition amount of the dihydrate gypsum was 0.01 mass parts (0.01 mass %) or more relative to 100 mass parts of the calcined gypsum, and furthermore, it was also able to be confirmed that the extent of increasing the value of the linear setting expansion was made possible to be controlled by controlling the addition amount of the dihydrate gypsum. Moreover, needless to say, a higher effect of increasing the value of the linear setting expansion as compared with Comparative Example where the copulverization was not conducted was obtained even in an addition amount of the dihydrate gypsum of 3 mass parts (3 mass %) relative to 100 mass parts of the calcined gypsum, however it was found that, in this case, the compressive strength was slightly lowered. Accordingly, with respect to the addition amount of the dihydrate gypsum to be added to the calcined gypsum in the present invention, although it depends on the intended use, it was found to be more preferable to add the dihydrate gypsum within a range of 2 mass parts (2 mass %) or less relative to 100 mass parts of the calcined gypsum taking the compressive strength into consideration when the gypsum composition is used for manufacturing a "non-clasp denture" or the like.

Example 2

<Study on Effects Obtained by Copulverization of Calcined Gypsum with Dihydrate Gypsum—Part 2>

Under the same pulverization conditions as in Example 1, 3 kg of the calcined gypsum and 6 g of the dihydrate gypsum were copulverized for a predetermined time, and the specific surface area and the value of the linear setting expansion [measured in accordance with Linear Setting Expansion (1) Measurement described in JIS T 6605 (2005)] were measured for the obtained gypsum composition.

(Evaluation Results)

The results obtained by conducting the above-described tests are shown in Table 3.

TABLE 1

Exploited Samples Obtained by Copulverizing Calcined Gypsum with Dihydrate Gypsum

| Dihydrate gypsum (external addition %) | 0 | 0.001 | 0.01 | 0.1 | 1.0 | 2.0 | 3.0 |
|---|---|---|---|---|---|---|---|
| Compressive strength (MPa) | 38 | 39 | 39 | 39 | 40 | 37 | 32 |
| Linear setting expansion value (%) | 0.378 | 0.431 | 0.477 | 1.041 | 1.064 | 1.071 | 1.082 |

TABLE 2

Comparative Samples Obtained by Adding Dihydrate Gypsum to Calcined Gypsum

| Dihydrate gypsum (external addition %) | 0 | 0.001 | 0.01 | 0.1 | 1.0 | 2.0 | 3.0 |
|---|---|---|---|---|---|---|---|
| Compressive strength (MPa) | 38 | 39 | 39 | 39 | 40 | 37 | 32 |
| Linear setting expansion value (%) | 0.378 | 0.382 | 0.398 | 0.433 | 0.531 | 0.622 | 0.708 |

TABLE 3

Relationship of Pulverization Time with Specific Surface Area and Expansion Coefficient of Gypsum Composition

| Pulverization time (min) | 0 | 10 | 30 | 60 | 120 | 180 | 480 |
|---|---|---|---|---|---|---|---|
| Specific surface area (cm$^2$/g) | 2260 | 2360 | 2460 | 2630 | 2960 | 3280 | 5040 |
| Linear setting expansion value (%) | 0.362 | 0.399 | 0.489 | 0.591 | 0.818 | 1.051 | 1.524 |

From Table 3, the effect of improving the value of the linear setting expansion was confirmed from 10 minutes after the start of the pulverization. The value of the specific surface area at 10 minutes after the start of the pulverization became larger by only about 100 cm$^2$/g as compared with that for the gypsum composition obtained without the pulverization. The specific surface area became larger as the pulverization time became longer, however the value of the linear setting expansion hit a peak at about 1.5%.

Examples 3 to 6 and Reference Example

<Test of Impression Property to Agar Impression Material for Fused Silica-Added High-Expansion Gypsum Composition>

Confirmation tests were conducted in the manner as described below for material systems each containing: a powdered gypsum composition material obtained by externally adding 0.2 mass parts of the dihydrate gypsum relative to 100 mass parts of the similar calcined gypsum as the calcined gypsum previously used; and further fused silica. First of all, powdered gypsum composition materials were each prepared by externally adding commercially available fused silica in a predetermined amount (1, 5, 10, 20, and 30 mass parts) relative to 100 mass parts of the total amount of the above-described calcined gypsum and dihydrate gypsum. And each of the powdered gypsum composition materials thus prepared was copulverized with the same ball mill as described previously under the same conditions as described previously for 3 hours to manufacture each high-expansion gypsum composition of Examples 3 to 6 and Reference Example. In order to verify the effect obtained by adding the fused silica, a powdered gypsum composition in which the fused silica was not added and 0.2 mass parts of the dihydrate gypsum was externally added was manufactured in the same manner as described above.

Gypsum slurries were each manufactured using each of the obtained high-expansion gypsum compositions and kneading each of the compositions with water, and each of the manufactured gypsum slurries was poured into a mold (impression) which was manufactured with an agar impression material and was obtained from a gypsum teeth model in the manner as described previously to manufacture a reproduction model of the teeth model. Then, the occurrence of cracks or not and the roughness on the surface of the reproduction model were observed by eye observation for each of the obtained reproduction models of the teeth model. The results are shown together in Table 4. The evaluation was conducted comparing with the case where the powdered gypsum composition in which the fused silica was not added was used, and the powdered gypsum composition in which the difference from the composition in which the fused silica was not added was not recognized by eye observation was evaluated as B. Moreover, the powdered gypsum composition in which the occurrence of cracks was clearly reduced by eye observation as compared with the case where the powdered gypsum composition in which the fused silica was not added was used was evaluated as A, and, in the similar manner, the powdered gypsum composition in which an improvement in roughness level on the surface was clearly recognized was evaluated as A.

TABLE 4

Comparison of Effects Obtained by Changing Addition Amount of Fused Silica

| | Example 3 | Example 4 | Example 5 | Example 6 | Reference Example |
|---|---|---|---|---|---|
| Addition amount of fused silica (external addition %) | 5 | 10 | 20 | 30 | 1 |
| Occurrence of cracks or not | A | A | A | A | B |
| Occurrence of roughness | A | A | A | A | B |

As shown in Table 4, it was found that the effect of adding the fused silica was not recognized in an addition amount of 1 mass % of the fused silica but that an addition amount of 5 mass % or more was enough for the effect to be recognized in terms of the occurrence of cracks or not in the reproduction models and the roughness on the surface of the reproduction models. In the case where 30 mass parts (30 mass %) of the fused silica was added, it was also confirmed that cracks and roughness on the surface in the reproduction models of the teeth model did not occur, however the addition of as large as 30 mass parts is not necessary when the material cost is taken into consideration.

Industrial Applicability

With the high-expansion gypsum composition provided as a utilization example of the present invention, a high expansion coefficient that has not been achieved in the conventional gypsum can be realized, and the expansion coefficient can appropriately be controlled using an inexpensive material, therefore, by utilizing the high-expansion gypsum composition, sophisticated shaping that is represented by a dental prosthesis which is used in dental treatment, is required to be sophisticated, and has a complicated shape becomes possible more simply and economically, and accordingly a wide range of utilization of the present invention is expected.

The invention claimed is:

1. A method for producing a high-expansion gypsum composition having an enhanced setting expansion coefficient, the method comprising:
a copulverizing step of copulverizing by a dry process a powdered gypsum composition material comprising calcined gypsum as a main component and dihydrate gypsum.

2. The method for producing a high-expansion gypsum composition according to claim 1, wherein the powdered gypsum composition material is obtained by externally adding the dihydrate gypsum within a range of 0.01 to 3 mass parts relative to 100 mass parts of the calcined gypsum.

3. The method for producing a high-expansion gypsum composition according to claim 1, wherein the powdered gypsum composition material further comprises fused silica, and the fused silica is externally added within a range of 5 to 30 mass parts relative to 100 mass parts of a total amount of the calcined gypsum and the dihydrate gypsum.

4. The method for producing a high-expansion gypsum composition according to claim 1, wherein a value of linear setting expansion for the gypsum composition after copulverization measured in accordance with Linear Setting Expansion (1) Measurement described in JIS T 6605 (2005) is increased 1.1 to 4.3 times as large as the value of the linear setting expansion for the powdered gypsum composition material before the copulverization by conducting the copulverization in the copulverizing step.

5. The method for producing a high-expansion gypsum composition according to claim 1, wherein the copulverization is conducted with a dry milling and pulverizing apparatus.

6. A high-expansion gypsum composition obtained by the method for producing a high-expansion gypsum composition according to claim 1, wherein a value of linear setting expansion measured in accordance with Linear Setting Expansion (1) Measurement described in JIS T 6605 (2005) is 0.45% or more.

7. A high-expansion gypsum composition obtained by the method for producing a high-expansion gypsum composition according to claim 1, wherein a value of specific surface area for the gypsum composition material after the copulverization is 2360 to 5040 $cm^2/g$.

8. The high-expansion gypsum composition according to claim 6, wherein the high-expansion gypsum composition is for being utilized for manufacturing a reproduction model of a teeth model to be used in forming a dental prosthesis.

* * * * *